US011007187B1

(12) United States Patent
Väänänen et al.

(10) Patent No.: US 11,007,187 B1
(45) Date of Patent: May 18, 2021

(54) MEDICINE FOR COVID-19 AND TREATMENT

(71) Applicant: Therapeutica Borealis Oy, Helsinki (FI)

(72) Inventors: Kalervo Väänänen, Turku (FI); Lauri Kangas, Lieto (FI); Matti Rihko, Turku (FI)

(73) Assignee: THERAPEUTICA BOREALIS OY, Helsinki (FI)

( * ) Notice: Subject to any disclaimer, the term of this patent is extended or adjusted under 35 U.S.C. 154(b) by 0 days.

(21) Appl. No.: 16/872,108

(22) Filed: May 11, 2020

Related U.S. Application Data

(60) Provisional application No. 63/015,345, filed on Apr. 24, 2020, provisional application No. 62/994,647, filed on Mar. 25, 2020.

(51) Int. Cl.
| | | |
|---|---|---|
| *A61K 31/4706* | (2006.01) | |
| *A61K 31/14* | (2006.01) | |
| *A61K 31/7048* | (2006.01) | |
| *A61K 38/57* | (2006.01) | |
| *A61K 31/24* | (2006.01) | |
| *A61K 9/00* | (2006.01) | |

(52) U.S. Cl.
CPC .......... *A61K 31/4706* (2013.01); *A61K 9/007* (2013.01); *A61K 9/0043* (2013.01); *A61K 31/14* (2013.01); *A61K 31/24* (2013.01); *A61K 31/7048* (2013.01); *A61K 38/57* (2013.01)

(58) Field of Classification Search
CPC .... A61K 31/4706; A61K 38/57; A61K 9/007; A61K 31/14; A61K 31/24; A61K 9/0043; A61K 31/7048; A61P 11/00; A61P 11/02; A61P 11/16; A61P 31/12
See application file for complete search history.

(56) References Cited

U.S. PATENT DOCUMENTS

| | | | | |
|---|---|---|---|---|
| 4,990,537 A * | 2/1991 | Okuyama | ............ | A61K 31/245 514/634 |
| 6,572,858 B1 * | 6/2003 | Charous | .................. | A61P 29/00 424/184.1 |
| 6,720,001 B2 * | 4/2004 | Chen | .................... | A61K 9/1075 424/455 |
| 6,930,125 B2 * | 8/2005 | Hunt | .................... | A61K 9/0078 514/172 |
| 7,183,112 B2 * | 2/2007 | Charous | ............. | A61K 31/4706 514/305 |
| 7,888,385 B2 * | 2/2011 | Hunt | .................... | A61K 9/0078 514/423 |
| 8,263,125 B2 * | 9/2012 | Vaya | .................... | A61K 9/2077 424/469 |
| 8,466,193 B2 * | 6/2013 | Verner | ....................... | A61P 1/04 514/427 |
| 8,637,469 B2 * | 1/2014 | Levitt | ................ | A61K 38/1709 514/21.2 |
| 8,906,954 B2 * | 12/2014 | Verner | ............... | A61K 31/4184 514/427 |
| 2004/0167162 A1 * | 8/2004 | Charous | ............. | A61K 31/4706 514/312 |
| 2014/0311482 A1 | 10/2014 | Levitt, Jr. | | |

FOREIGN PATENT DOCUMENTS

| | | | | | |
|---|---|---|---|---|---|
| WO | WO-2012026963 A2 * | 3/2012 | | .......... | A61M 11/041 |
| WO | WO-2013044871 A1 * | 4/2013 | | ............. | A61P 31/16 |

OTHER PUBLICATIONS

Ding et al., "Organ distribution of severe acute respiratory syndrome (SARS) associated coronavirus (SARS-CoV) in SARS patients : implications for pathogenesis and virus transmission pathways", 2004, Journal of Pathology, 203(2), pp. 622-630. (Year: 2004).*
Ziegler et al., "SARS-CoV-2 Receptor ACE2 Is an Interferon-Stimulated Gene in Human Airway Epithelial Cells and Is Detected in Specific Cell Subsets across Tissues", May 28, 2020, Cell, 181(5), pp. 1016-1035. (https://doi.org/10.1016/j.cell.2020.04.035) (Year : 2020).*
Sungnaket al.,"SARS-CoV-2 entry factors are highly expressed in nasal epithelial cells together with innate immune genes", May 2020, Nature Medicine, 26(5), pp. 681-687. (Year: 2020).*
National Institutes of Health (NIH) press release, Jun. 20, 2020, "NIH halts clinical trial of hydroxychloroquine", pp. 1-2. (https://www.nih.gov/news-events/news-releases/nih-halts-clinical-trial-hydroxychloroquine) (Year: 2020).*
Cavalcanti et al., "Hydroxychloroquine with or without Azithromycin in Mild-to-Moderate Covid-19", Jul. 2020, The New England Journal of Medicine, pp. 1-12. (DOI: 10.1056/NEJMoa2019014) (Year: 2020).*
Magagnoli et al., "Outcomes of Hydroxychloroquine Usage in United States Veterans Hospitalized with COVID-19", Nov. 2020 , Med, vol. 1, pp. 1-14. (https://doi.org/10.1016/j.medj.2020.06.001) (Year: 2020).*
National Center for Biotechnology Information. "PubChem Compound Summary for CID 14013, Ammonium bicarbonate" PubChem, https://pubchem.ncbi.nlm.nih.gov/compound/Ammonium-bicarbonate. Create Jul. 19, 2005. Accessed Dec. 2, 2020. (Year: 2005).*

(Continued)

*Primary Examiner* — My-Chau T. Tran
(74) *Attorney, Agent, or Firm* — Patterson + Sheridan, LLP

(57) ABSTRACT

The invention concerns a medicine and a prophylactic medicine for COVID-19 disease. The inventive medicine targets the endosomic, non-endosomic and/or intracellular viral pathways and inhibits them. The best mode of the invention is considered to be the medicine that blocks all three viral pathways. In the best mode the individual dose of a constituent component of the medicine is arranged to a dosage size sufficient to inhibit its designated SARS-CoV-2 viral pathway. This allows the dose of a particular pharmacological agent to be smaller than in a drug with just one kind of pharmacological agent. The best mode of the invention shuts the two cell membrane viral pathways and the one intracellular viral pathway with the minimum efficient dose, thereby preventing drug overdose, and enabling prophylactic or preventive use.

4 Claims, 8 Drawing Sheets

(56) References Cited

OTHER PUBLICATIONS

Figure 1:
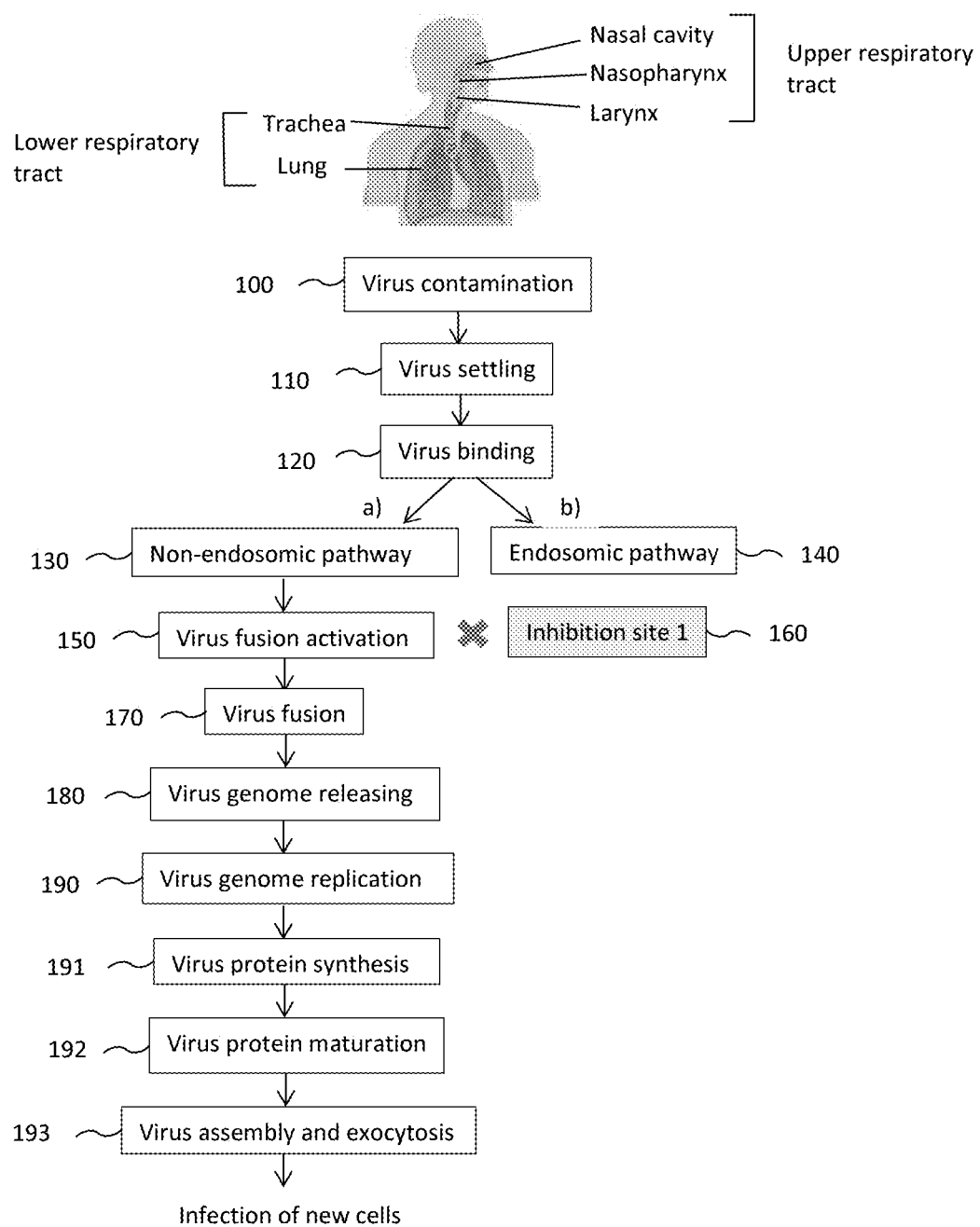

Millet, J.K., Whittaker, G.R., 2018. Physiological and molecular triggers for SARS-CoV membrane fusion and entry into host cells. Virology 517, 3-8.
Zumla, A., Chan, J.F.W., Azhar, E.I., Hui, D.S.C., Yuen, K-Y., 2016. Coronaviruses—drug discovery and therapeutic options. Nat. Rev. Drug Discov. 15, 327-347.
Farsalinos, K. et al., "Systematic review of the prevalence of current smoking among hospitalized COVID-19 patients in China: could nicotine be a therapeutic option?," Intern Emerg Med. 2020;1-8.
Farsalinos, K. et al., "Editorial: Nicotine and SARS-CoV-2: COVID-19 may be a disease of the nicotinic cholinergic system," Toxicol Rep. 2020;7:658-663.

* cited by examiner

20

Upper respiratory tract:
- Nasal cavity
- Nasopharynx
- Larynx

Lower respiratory tract:
- Trachea
- Lung

- Virus contamination — 200
- Virus settling — 210
- Virus binding — 220
  - a) Non-endosomic pathway — 230
  - b) Endosomic pathway — 240
- Uptake into endosomes — 250
- Inhibition site 2 — 270 ✖ Endosome acidification — 260
- Virus fusion — 280
- Virus genome releasing — 290
- Virus genome replication — 291
- Virus protein synthesis — 292
- Virus protein maturation — 293
- Virus assembly and exocytosis — 294
- Infection of new cells

Fig. 2

MEDICINE FOR COVID-19 AND TREATMENT

FIELD OF THE INVENTION

The invention concerns a medicine and a prophylactic medicine for COVID-19.

BACKGROUND

Viruses are incapable of free-living existence. They can infect cells and cause various diseases by invading cells and redirecting the synthetic machinery of mammalian cells toward the production of more virus particles. Viruses can enter cells via different mechanisms.

In case of respiratory viral diseases, viruses enter body usually via the epithelial cells of respiratory track. Accompanying FIGS. 1-3 and 7 show anatomical structure of human respiratory track. Often viruses enter the body already through epithelial cells in upper respiratory track, for instance via nasal mucosa. This is true especially if viruses are delivered by accident via hands to nasal mucosa.

When the virus has reached the surface of respiratory epithelium, it must enter the cell in order to propagate the disease.

First, the virus needs a specific cellular receptor on plasma membrane. Several specific receptors for different viruses are known. However, usually each virus has only one specific type of receptor on the target cell membrane. Receptors could be proteins, carbohydrate moieties or even membrane lipids. In case of influenza A the virus specific receptor is alpha-2,6-sialic acid and in case of SARS-Cov and SARS-Cov-2 the specific receptor is the ACE2 protein.

After binding of the virus to the specific membrane protein, for example, this binding induces a cascade of molecular events that eventually lead to the release of viral genome into the host cell cytoplasm. The presence of a specific receptor on the cell surface is usually needed for viral entrance. After binding to the cell membrane, different viruses can induce one or even more molecular mechanisms to enter the cellular cytoplasm as indicated in accompanying figures.

SARS-Cov-2 virus that induces human Covid-19 disease can either perform a so-called early entry (FIGS. 1 and 4) or late entry (FIGS. 2 and 5) into cellular cytoplasm.

In the early entry, specific cellular proteases are needed to cleave the viral protein, which will activate the fusion of viral envelope to the cell membrane and lead to entry of viral nucleocapsid into cellular cytoplasm.

In case of influenza and corona viruses, activating proteases could be at least transmembrane protease serine Si member and human trypsin like protease. In addition to endogenous proteases, also other proteases secreted into the luminal space could induce cleavage and activate the fusion of virus envelope to the plasma membrane.

Enveloped viruses like influenza and corona viruses can enter the epithelial cells also via receptor-mediated endocytosis and release viral content in late endosomes. This type of entry does not need proteases on the cell surface.

In this type of endosome entrance into cytoplasm virus attaches to a specific type membrane receptor and this binding induces so called receptor-mediated endocytosis. Virus particles are taken first into early endosomes and during maturation of these towards late endosomes, and the interiors of these vesicles becomes acidic via action of membrane bound vacuolar ATPase. This acidification activates endosomal proteases, like cathepsin L. Activated proteases are able to cleave viral envelope inducing fusion of virus to the late endosome's membrane and leading to the release of viral genome into cellular cytoplasm.

After releasing of viral genome into the cytoplasm, copying the genome with reverse transcriptase enzyme (depending on the genomic material type), synthesizing virus genome and proteins by cellular machinery, virus genome and virus proteins are assembled to form new viruses, which can then propagate the infection further. Viral protein genes are translated to proteins via cellular protein synthesis machinery in endoplasmic reticulum and Golgi complex.

It is known in the art that people who work with cattle rarely contract influenza.

Washing hands with soap is also known to be a good strategy to prevent viruses.

Four human coronavirus strains (HCoV-229E, HCoV-OC43, HCoV-NL-63 and HCoV-HKU1) are known in the art, which cause mild upper respiratory tract infections. However, during last 20 years two new zoonotic coronaviruses have appeared, MERS-CoV (Middle East respiratory syndrome coronavirus) and SARS-CoV (severe acute respiratory syndrome coronavirus). By contrast to human coronaviruses, these can cause more severe disease symptoms, mainly in respiratory organs, but also extrapulmonary complications. In 2019 a third zoonotic coronavirus emerged, SARS-CoV-2 causing the COVID-19 disease (also called COVID-19 virus).

J. K Millet and G. R. Whittaker, Physiological and molecular triggers for SARS-CoV membrane fusion and entry into host cells, Virology 517, 3-8 (2018), describes the strategies of coronavirus entry into cells. Coronavirus enters into cell by two alternative routes: non-endosomic and/or endosomic pathways. In non-endosomic entry virus particle attaches to host cell membrane through virus surface S protein (spike) and specific cell membrane ACE2 (angiotensin-converting enzyme) receptor interaction. Then S protein fuses virus envelope to cell membrane by the aid of cell proteinases in a pH independent way, virus enters into cell, dissembles and releases its genome (RNA) into cytoplasm. Thereafter the released uncoated RNA is replicated by reverse transcriptase enzyme and virus protein synthesis and replication of new virus genomic RNA starts and proceeds by host's cellular machinery. Virus proteins are transported through endoplasmic reticulum/Golgi apparatus, where they mature in pH dependent conditions, e.g. by glycosylation. Then virus particles are assembled from virus proteins and virus RNA genome in the cytoplasm to new infectious viruses. Finally, viruses are released from the cell by exocytosis and infect new cells. In endosomic entry, virus particle attaches to host cell membrane also through virus surface S protein (spike) and specific cell membrane ACE2 receptor interaction, like above. After that, the virus is taken into cell early endosome by clathrin-mediated endocytosis. When early endosome acidifies to mature late endosome, virus fuses to endosome's membrane through S protein/ACE2 interaction and by the aid of cellular proteinases. Then RNA genome is released into cytoplasm, and from this point, the production and maturation of virus particles are identical to non-endosomic pathway. These strategies are depicted in more detail in accompanying figures.

There are many stages, where the entry of the virus, the release of its genome and its maturation can be prevented, although currently there is no antiviral treatment effective for coronaviruses. At the time of writing, there is a suspicion that Remdesivir developed by Gilead Sciences might have some efficacy against the coronavirus in very ill patients, reducing the time spent per patient in Intensive Care Units ICU.

A. Zumla, et al., *Coronaviruses—drug discovery and therapeutic options*, Nat. Rev. Drug Discov. 15, 327-34 (2016) reviews numerous therapeutic interventions suggested and studied in clinical trials. These include e.g. virus-based strategies to disturb/prevent replication of the virus RNA genome, to inhibit synthesis and function of different virus proteins and to prevent virus S protein/cell ACE2 receptor interaction, or host-based strategies to induce host's immune response, to prevent host signaling pathways involved in virus replication, to inhibit virus entry by blocking cellular receptors or by inhibiting the function of cellular membrane and endosomal proteins, by disturbing endocytosis or by modifying cell's pH levels at different stages. Also, studies to develop vaccines have been numerous and extensive by different design strategies, but with no clinical success yet.

U.S. Patent Publication No. 2014/0311482 lists a broad catalogue of treatments that can be administered with a broad array of drug delivery strategies. It relates to the treatment of upper airway infections with proinflammatory cytokine inhibitors and other bioactive agents, like antiangiogenic, anti-inflammatory, antibiotic, antiviral, antifungal and antiprotozoal compounds, focusing on their usage in the treatment of sinusitis. In addition, it describes the use of different drug delivery systems for local noninvasive administration of the drugs to nasopharyngeal tract. These include nasal administration e.g. by sprays, aerosols, gels, solutions, emulsions and suspensions, and with the aid of targeting delivery devices, like nasal inhalers, aerolizers and microcatheters.

In the prior art both the intracellular and the extracellular pathways with which coronavirus interacts with the mammalian cells are reasonably well understood. There are several studies and trials going on to develop new drugs and vaccines to prevent or treat COVID-19, but no effective cure or preventive measure for it has yet been found.

SUMMARY

Figure 4:
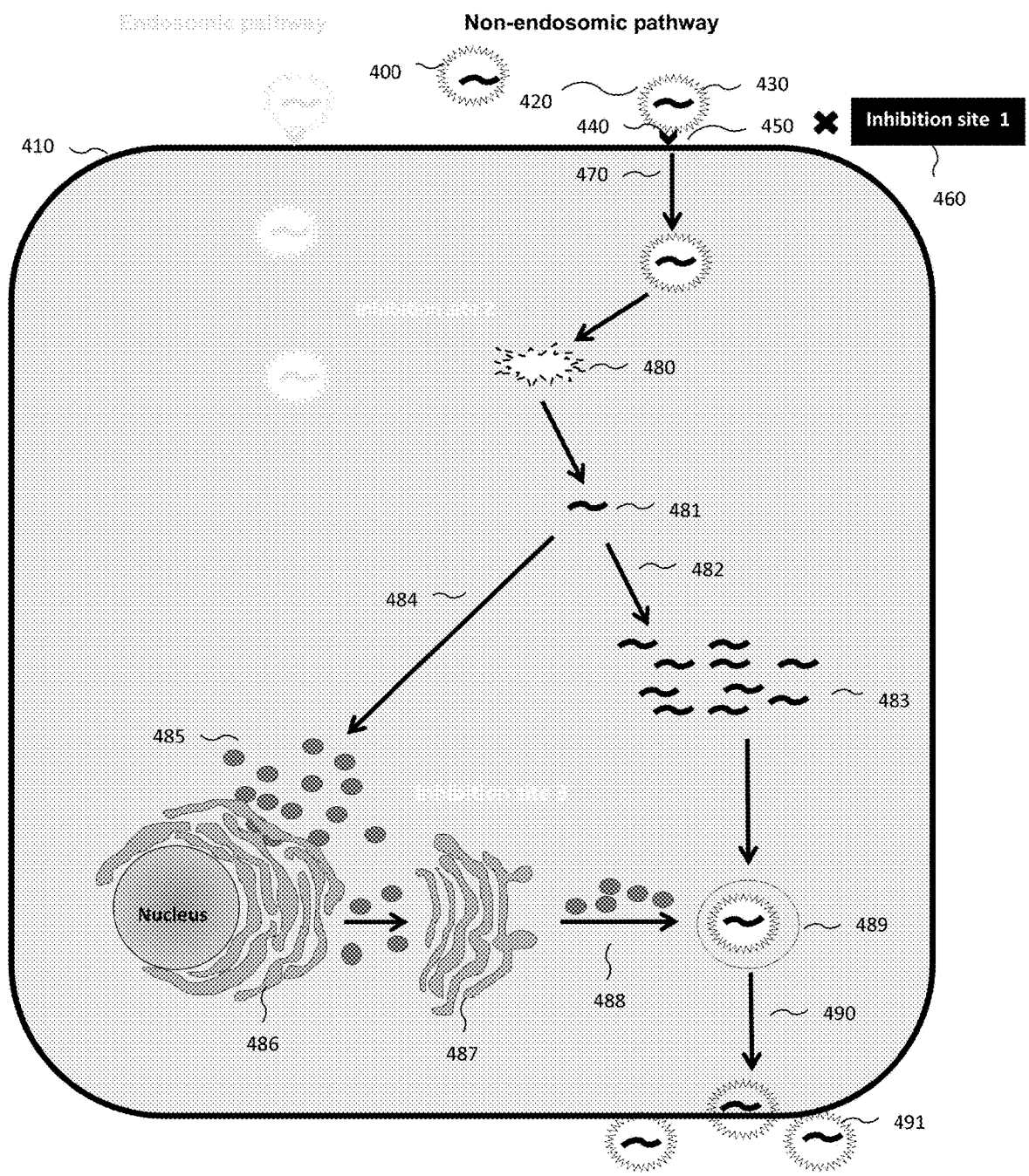

One aspect of the invention is a medicine that comprises at least one protease inhibitor arranged to inhibit the fusion of the COVID-19 virus through the plasma membrane of a mammalian respiratory cell (see inhibition site 1, FIGS. 1 and 4).

Another second aspect of the invention is a medicament for altering the pH of the mammalian respiratory cell endosomal interior in order to inhibit the passage of the COVID-19 through the endosomal membrane into the cell cytoplasm.

In one embodiment, the pH is increased, so that the environment of the endosome is more basic. In one embodiment, the medicine is a nasal spray, such as chloroquine phosphate.

Alternative drug administration methods include orally consumed pills, chewing gum and/or creams or any other local application method that increases the pH in the respiratory cell membranes and endosomes.

Alternative embodiments may use hydroxychloroquine phosphate and/or chloroquine phosphate and/or chloroquine sulphate and/or hydroxychloroquine sulphate as the pH increase inducing agent.

The activation of late endosomal proteases can be inhibited by preventing acidification of endosomes. This could be done by weak bases like chloroquine, ammonium salts or by blocking vacuolar ATPase by proton pump inhibitors, like bafilomycin. Acidification can also be disturbed by affecting ion channels, e.g. glutamate gated chloride channels, by ivermectin.

Figure 5:
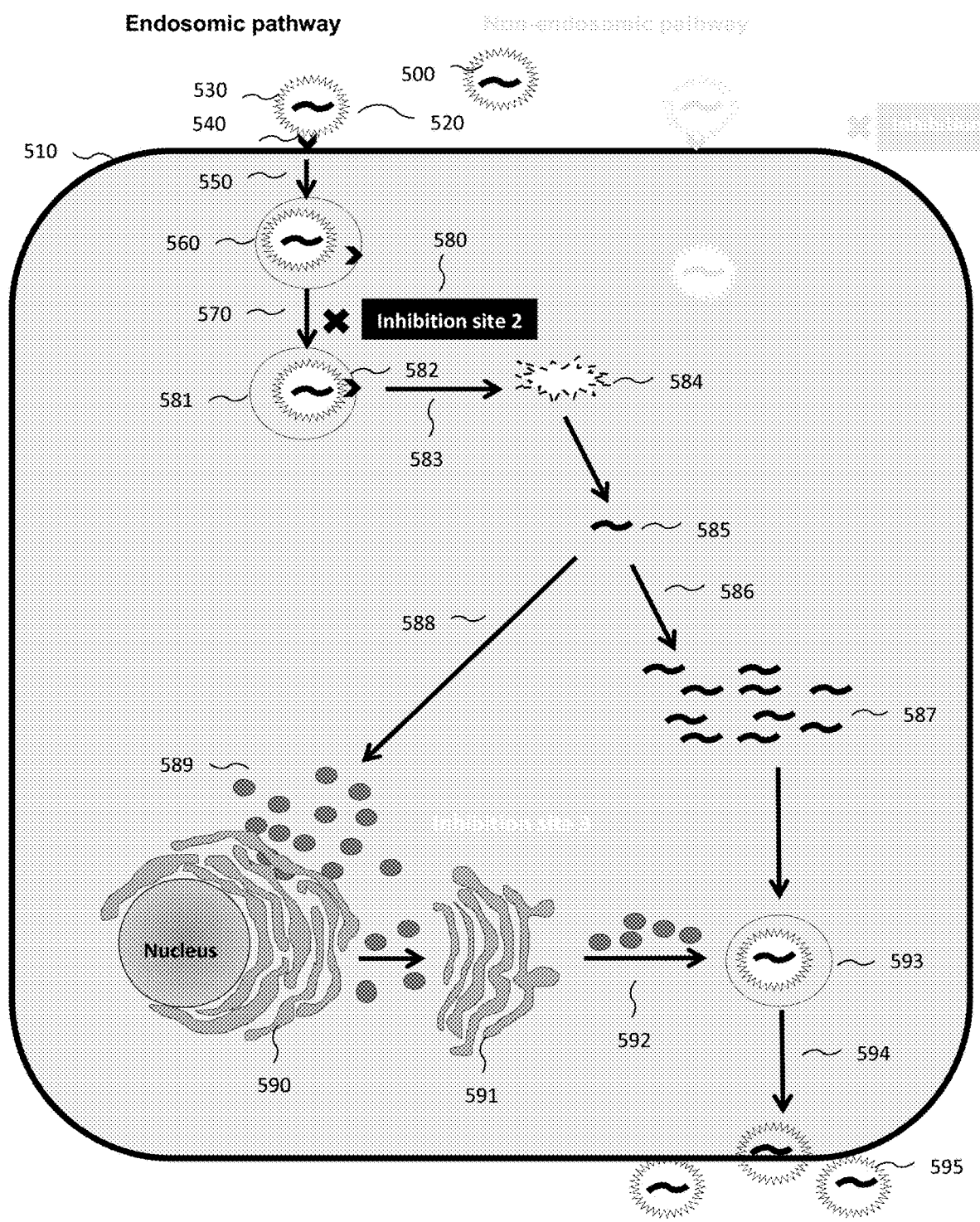

The inhibition of endosomal acidification can thus prevent replication of viruses via receptor-mediated endocytosis (see inhibition site 2, FIGS. 2 and 5).

In another third aspect of the invention in late compartments of Golgi complex, slightly acidic pH is needed for proper glycosylation of proteins. In virus-infected cells, basically all protein synthesis serves production of viral proteins. If one could prevent acidification of the trans-Golgi network of infected cells, the infected cells would not be able to glycosylate viral proteins correctly. This acidification can be prevented by weak bases and vacuolar proton pump inhibitors, and thus giving another possibility to inhibit new virus formation (see inhibition site 3, FIGS. 3 and 6). This block will inhibit synthesis of viral proteins entering cells by all possible pathways.

A medicine for COVID-19, characterized in that, the medicine comprises at least one protease inhibitor arranged to inhibit the fusion of the COVID-19 virus through the plasma membrane of a mammalian respiratory cell.

A medicine for COVID-19 is in accordance with the invention and characterized in that, the medicine is a pH increase inducing agent, and said medicine is administered to a patient to inhibit endosomal acidification, thereby preventing cathepsin activation and inhibiting fusion of viral envelope to the endosomal membrane thus preventing release of SARS-CoV-2 viruses into the cytoplasm and the consequent replication of SARS-CoV-2 viral RNA in the mammalian respiratory cell.

A medicine for COVID-19, characterized in that, the medicine is arranged to target viral RNAs in the endoplasmic reticulum, and the viral RNAs are arranged to be translated to viral proteins, and the viral proteins are arranged to be transported into the Golgi compartment of the mammalian respiratory cell, where the viral proteins are arranged to be glycosylated, and the medicine is arranged to inhibit any of the preceding reactions and/or arranged to inhibit proton pumps.

A medicine for COVID-19 is in accordance with the invention and is characterized in that, the medicine is a pH increase inducing agent, and said medicine is administered to a patient to inhibit endosomal acidification preventing cathepsin activation and thus inhibit fusion of viral envelope to the endosomal membrane preventing release of SARS-CoV-2 viruses into the cytoplasm, and the consequent replication of SARS-CoV-2 viral RNA in the mammalian respiratory cell, and the medicine comprises protease inhibitors arranged to inhibit the fusion of the SARS-CoV-2 virus through the plasma membrane of a mammalian respiratory cell, and the medicine is arranged to target viral RNAs in the endoplasmic reticulum, and the viral RNAs are arranged to be translated to viral proteins, and the viral proteins are arranged to be transported into the Golgi compartment of the mammalian respiratory cell, where the viral proteins are arranged to be glycosylated, and the medicine is arranged to inhibit any of the preceding reactions and/or arranged to inhibit proton pumps.

The invention has great advantages in that it can be used to prevent a COVID-19 infection when social contact is unavoidable and/or necessary. Because the inventive medicine is targeted to all viral pathways, the absolute doses of the constituent medicines can be small, thus allowing long term use even for people who might be sensitive to the constituent medicines in normal doses. This allows healthcare workers, such as doctors and nurses, to consume the inventive medicine all the time when they are in contact with patients. The medicine also has the advantage over hygienic measures in that the effect is on all the time. Many healthcare workers who have worn protective gear have fallen ill, because the coronavirus has "leaked" through the protective gear.

The best mode of the invention is considered to be the medicine that blocks all three viral pathways. In the best mode, the individual dose of a constituent component of the medicine is arranged to a dosage size sufficient to inhibit its designated SARS-CoV-2 viral pathway. This allows the dose of a particular pharmacological agent to be smaller than in a drug with just one kind of pharmacological agent. The best mode of the invention shuts the two plasma membrane viral pathways and the one intracellular viral pathway with minimum efficient dose, thereby preventing drug overdose, and enabling prophylactic or preventive use.

BRIEF DESCRIPTION OF THE DRAWINGS

FIG. 1 shows the anatomical structure of human respiratory tract. It also describes the virus entry via non-endosomic pathway into a mammalian respiratory cell cytoplasm as an embodiment 10 as a flow diagram, and the inventive medicine impact to said viral pathway, in accordance with the invention (inhibition site 1, phase 160).

FIG. 2 shows the anatomical structure of human respiratory tract. It also describes the virus entry via endosomic pathway into a mammalian respiratory cell cytoplasm as an embodiment 20 as a flow diagram, and the inventive medicine impact to said viral pathway, in accordance with the invention (inhibition site 2, phase 270).

FIG. 3 shows the anatomical structure of human respiratory tract. It also describes the virus intracellular viral pathway in the endoplasmic reticulum and Golgi complex of a mammalian cell as an embodiment 30 as a flow diagram, and the inventive medicinal impact to this viral pathway, in accordance with the invention (inhibition site 3, phase 391).

FIG. 4 describes the virus entry via non-endosomic pathway into a mammalian respiratory cell cytoplasm as an anatomic diagram, and the inventive medicine impact to said viral pathway embodiment 40, in accordance with the invention (inhibition site 1, 460).

FIG. 5 describes the virus entry via endosomic pathway into a mammalian respiratory cell cytoplasm as an anatomic diagram, and the inventive medicine impact to said viral pathway as embodiment 50, in accordance with the invention (inhibition site 2, 580).

FIG. 6 describes the virus intracellular viral pathway in the endoplasmic reticulum and Golgi complex of a mammalian cell as an anatomic diagram, and the inventive medicinal impact to this viral pathway as an embodiment 60, in accordance with the invention (inhibition site 3, 670).

FIG. 7 shows the anatomical structure of human respiratory tract. It also describes the non-endosomic, endosomic, and intracellular viral pathways together to provide a functional presentation on how these pathways and the respective inventive medicinal impact on these pathways operate simultaneously in a mammalian cell as a flow diagram in embodiment 70 (inhibition sites 1, 2 and 3, phases 760, 790 and 796, respectively).

FIG. 8 describes the non-endosomic, endosomic, and intracellular viral pathways together to provide an anatomic presentation on how these pathways and the respective inventive medicinal impact on these pathways operate simultaneously in a mammalian cell as an embodiment 80 (inhibition sites 1, 2 and 3, phases 860, 884 and 895, respectively).

Some embodiments of the invention are described in the dependent claims.

DETAILED DESCRIPTION

The invention is illustrated in more detail in the following figures.

FIG. 1 displays the embodiment 10, where in phase 100 enveloped viruses, like coronavirus, enter and contaminate the respiratory track either via direct contact of fingers or other virus carrying surfaces or via inhaled air. Virus can enter nasopharyngeal area through nose, mouth or eyes having a direct contact to nasal cavity. From upper airways, it can emanate downwards in the respiratory tract, and in more severe cases into lungs causing pneumonia. In some cases, it can go even to stomach causing e.g. diarrhea.

In phase 110 after contamination 100 virus approaches and settles down on respiratory track mucosa. To initiate infection virus has to enter into epithelial cells of the respiratory mucosa.

In phase 120 after settling 110 on cell membrane, virus binds to a specific receptor on the surface of respiratory track epithelial cells. Each enveloped virus has its own specific receptor for binding. For SARS-CoV-2 this receptor is ACE2 membrane protein. E.g. for influenza it is alpha-2,6-sialic acid. In the case of SARS-CoV-2, this binding happens through virus surface S protein (spike) and cell membrane ACE2 receptor interaction.

After SARS-CoV-2 virus binding 120 to cell membrane receptor, two alternative pathways 130 and 140 can be initiated: a) non-endosomic pathway 130 (endocytosis independent pathway), orb) endosomic pathway 140 (endocytosis dependent pathway). Depending on the virus, for the entry into cell, it can use either pathways a) or b); in the case of coronavirus, it can use both of them.

The embodiment 10 describes the pharmaceutical effect of the invention on the non-endosomic pathway 130. In the non-endosomic pathway (a) 130 membrane protease, e.g. transmembrane protease serine subfamily 2 (TMPRSS2), activates the ACE2 receptor and virus S protein for fusion in phase 170 in pH independent manner. This activation can be inhibited at inhibition site 1 160 by protease inhibitors, e.g. camostat and aprotinin. This is the reason that the inventive medicine preferably contains meaningful doses of protease inhibitors, e.g. camostat and aprotinin.

In phase 170 protease activates a fusion peptide part in the virus S protein, which then fuses virus envelope into the cell membrane.

In phase 180, after fusion 170, virus nucleocapsid enters into cell cytoplasm and dissembles, whereby virus genetic material is released. In the case of coronaviruses, the genetic material is a single-stranded RNA genome.

In phase 190 after genome releasing 180 of virus genome, the virus genome replicates by reverse transcriptase enzyme in the case of SARS-Cov-2, produced by host cell's protein synthesis machinery.

In phase 191 viral proteins and RNA genome of SARS-CoV-2 are synthesized using host cell's own protein synthesis machinery. At this point virus 'kidnaps' for its use the whole protein producing capacity of the cell and most of the products synthesized are viral (proteins, RNA).

In phase 192 after viral protein synthesis 191, the viral proteins are maturated in host cell's endoplasmic reticulum/Golgi compartment, e.g. by glycosylation. Some of these protein maturation reactions in Golgi apparatus are pH dependent (acidic).

In phase 193, after viral protein maturation 192, these viral proteins and new genomic viral RNA molecules 190 are assembled in the cytoplasm to give rise to new infectious virus particles. After assembly, virus particles are released from the cell by exocytosis and initiate the infection cycle in new cells.

The inventive medicine targets the virus fusion phase 170 and the virus fusion activation phase 150 by providing viral fusion inhibiting protease inhibitors, e.g. camostat and aprotinin. When phases 150 and 170 become inactive, the virus production machine of the host cell phases (180, 190, 191, 192, 193) does not start, as new SARS-CoV-2 viruses cannot enter via the non-endosomic pathway 130. These protease inhibitor compounds are preferably locally administered to the patients by means of any of the following: Nasal drops, nasal sprays or aerosols targeted into lower respiratory pathway, either alone or in combinations. For example, in some embodiments the inventive medicine could be vaporized or provided as an aerosol through the air conditioning system or air ventilation system of a building, for example a hospital.

However, the SARS-CoV-2 can still enter the host cell via the endosomic pathway and this is discussed in FIG. 2, embodiment 20.

Embodiment 10 can be readily combined with embodiments 20, 30, 40, 50, 60, 70, 80 and/or 90, because the intracellular and extracellular pathways described therein are in use simultaneously in a mammalian respiratory cell, in accordance with the invention.

In FIG. 2 phase 200 the coronavirus enters and contaminates the respiratory track. The coronavirus obtains access either via direct contact of fingers or via direct contact form other virus carrying surfaces or via inhaled air. Virus can enter nasopharyngeal area through nose, mouth or eyes having a direct contact to nasal cavity. From upper airways, it can emanate downwards in the respiratory tract, and in more severe cases into lungs causing pneumonia. In some cases, it can go even to stomach causing e.g. diarrhea.

In phase 210, after contamination 200 virus approaches and settles down on respiratory track mucosa. To initiate infection virus has to enter into epithelial cells of the respiratory mucosa.

In phase 220 after settling in phase 210 on cell membrane, virus binds to specific receptor on the surface of respiratory track epithelial cells. Each enveloped virus has its own specific receptor for binding. For SARS-CoV-2 this receptor is ACE2 membrane protein. In the case of SARS-CoV-2 this binding happens through virus surface S protein (spike) and cell membrane ACE2 receptor interaction.

After virus binding 220 to cell membrane receptor, two alternative pathways 230 and 240 can be initiated: a) non-endosomic pathway 230 (endocytosis independent pathway), or b) endosomic pathway 240 (endocytosis dependent pathway). This embodiment 20 focuses on the endosomic pathway. Depending on the virus, for the entry into cell, it can use either pathways a) or b); in case of coronavirus, it can use both of them.

In phase 250 in endosomic pathway (b) 240 after virus has bound to ACE2 on cell membrane, ACE2/virus complex is transferred into an early endosome through a clathrin-mediated endocytosis.

In cytoplasm, the early endosome is acidified and matures to late endosome. This acidification in phase 260 can be inhibited at inhibition site 2 in phase 270 by weak bases, like ammonium salt, ammonium chloride, ammonium bicarbonate and chloroquine, by vacuolar ATPase inhibitors, like bafilomycins and diphyllin, or by ion channel modulators, like ivermectin. The inventive medicine preferably comprises any of the aforementioned compounds in meaningful doses to inhibit the endosome acidification, and the transport of the ACE2/SARS-CoV-2 complex within the endosome.

In phase 280 acidification of the endosome 260 causes the virus to fuse to endosome membrane through the interaction of ACE2 receptor and virus S protein fusion peptide activated by protease, like cathepsin, in acidic pH conditions.

In phase 290 after fusion 280, virus nucleocapsid enters into cell cytoplasm and dissembles, whereby virus genetic material is released. In the case of coronaviruses, the genetic material is a single-stranded RNA genome.

In phase 291 after genome releasing 290 of virus genome, it replicates by reverse transcriptase enzyme in the case of SARS-Cov-2, produced by host cell's protein synthesis machinery.

In phase 292 viral proteins and RNA genome, in the case of SARS-CoV-2, are synthesized using host cell's own protein synthesis machinery. At this point SARS-CoV-2 'kidnaps' for its use all or some of the protein producing capacity of the cell and most of the products synthesized are viral proteins and viral RNA.

In phase 293 after viral protein synthesis 292, they are maturated in host cell's endoplasmic reticulum/Golgi compartment, e.g. by glycosylation. Some of these protein maturation reactions in Golgi apparatus are pH dependent (acidic).

In phase 294 after viral protein maturation 293, they and new genomic viral RNA molecules 291 are assembled in the cytoplasm to form new infectious virus particles. After assembly, virus particles are released from the cell by exocytosis and can initiate the infection cycle in new cells.

When phase 260 becomes inactive, the virus production machine of the host cell phases (280, 290, 291, 292, 293) does not start, as new SARS-CoV-2 viruses cannot enter via the endosomic pathway 240. These weak bases, vacuolar ATPase inhibitors and/or by ion channel modulators compounds are preferably locally administered to the patients by means of any of the following: Nasal drops, nasal sprays or aerosols targeted into lower respiratory pathway, either alone or in combinations. For example, in some embodiments the inventive medicine could be vaporized or provided as an aerosol through the air conditioning system or air ventilation system of a building, for example a hospital.

Even more preferably the weak bases, like ammonium bicarbonate and chloroquine, by vacuolar ATPase inhibitors, like bafilomycins and diphyllin, or by ion channel modulators, like ivermectin of phase 270 are mixed together with protease inhibitors, such as camostat and aprotinin, used in phase 130 of embodiment 10. This will preferably lead to complete blocking of SARS-CoV-2 viruses from the respiratory cells, as the SARS-CoV-2 cannot penetrate the cell membrane of the respiratory cell. The doses of each of the aforementioned compounds should preferably be set to a level, that results in complete SARS-CoV-2 blocking. However, dosages at that level might be unattainable in some patients, and there may be some random error in that no matter what the doses at inhibiting phases 130, 270, some SARS-CoV-2 viruses manage to enter the cytoplasm. Or worse, there might be a third yet undiscovered extracellular pathway that we do not presently know about.

Figure 3:
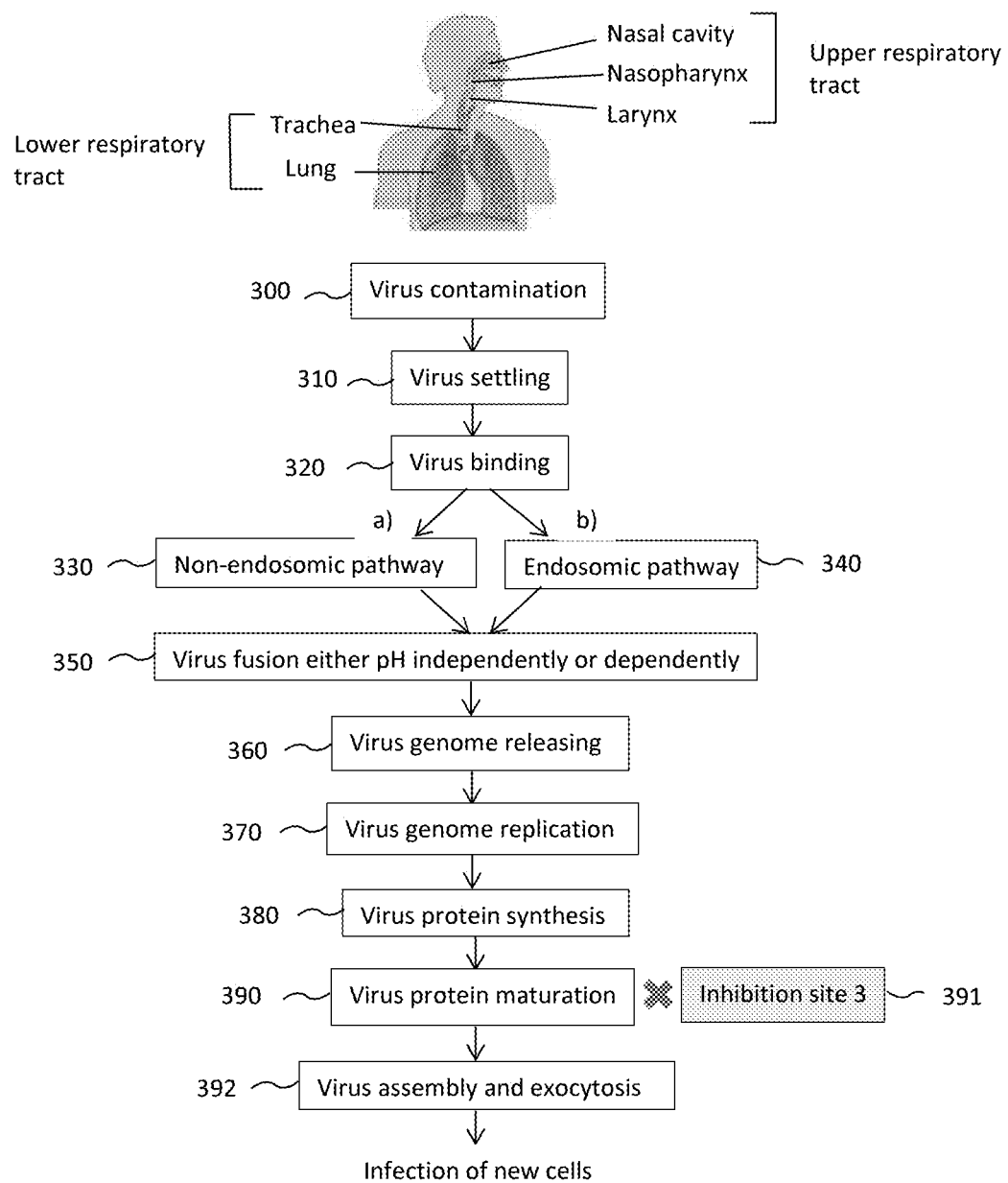

Therefore, we will look at an inventive intracellular inhibiting mechanism in FIG. 3, embodiment 30.

Embodiment 20 can be readily combined with embodiments 10, 30, 40, 50, 60, 70, 80 and/or 90, because the intracellular and extracellular pathways described therein are in use simultaneously in a mammalian respiratory cell, in accordance with the invention.

In FIG. 3 embodiment 30 enveloped viruses, like the coronavirus, enter and contaminate the respiratory track either via direct contact of fingers or other virus carrying surfaces or via inhaled air. Virus can enter nasopharyngeal area through nose, mouth or eyes having a direct contact to nasal cavity. From upper airways, it can emanate downwards in the respiratory tract, and in more severe cases into lungs causing pneumonia. In some cases, it can go even to stomach causing e.g. diarrhea.

In phase 310 after contamination 300 virus approaches and settles down on respiratory track mucosa. To initiate infection virus has to entry into epithelial cells of the respiratory mucosa.

In phase 320 after settling in phase 310 on cell membrane, SARS-CoV-2 virus binds to specific receptor on the surface of respiratory track epithelial cells. Each enveloped virus has its own specific receptor for binding. For SARS-CoV-2 this receptor is ACE2 membrane protein, and e.g. for influenza it is alpha-2,6-sialic acid. In the case of SARS-CoV-2, this binding happens through virus surface S protein (spike) and cell membrane ACE2 receptor interaction.

After virus binding 320 to cell membrane receptor, two alternative pathways 330 and 340 can be initiated: a) non-endosomic pathway 330 (endocytosis independent pathway), or b) endosomic pathway 340 (endocytosis dependent pathway). Depending on the virus, for the entry into cell, it can use either pathways a) or b); in case of SARS-CoV-2, it can use both of them.

In phase 350 the SARS-CoV-2 nucleocapsid fuses to cell membranes either in pH independent way 170 to cell membrane or in pH dependent way 280 to endosomal membrane.

In phase 360, after fusion 350, the SARS-CoV-2 virus nucleocapsid enters into cell cytoplasm and dissembles, whereby viral genetic material is released. In the case of SARS-CoV-2, the genetic material is a single-stranded RNA genome.

In phase 370 after genome releasing in phase 360 of SARS-CoV-2 virus genome, it replicates by reverse transcriptase enzyme produced by host cell's protein synthesis machinery.

In phase 380 viral proteins and RNA genome, in the case of SARS-CoV-2, are synthesized using host cell's own protein synthesis machinery. At this point SARS-CoV-2 virus tries to 'kidnap' for its use the whole protein producing capacity of the cell which would lead to most of the products being synthesized being viral (proteins, RNA).

After viral protein synthesis 380 they are maturated in host cell's endoplasmic reticulum/Golgi compartment, e.g. by glycosylation. Some of these protein maturation reactions in Golgi apparatus are pH dependent (acidic). This maturation can be inhibited at inhibition site 3 in phase 391 by weak bases, like ammonium salt, ammonium chloride, ammonium bicarbonate and chloroquine. Also, vacuolar ATPase inhibitors, like bafilomycins and diphyllin, or ion channel modulators, like ivermectin, can be used in inhibiting this step. The inventive medicine preferably comprises any of the aforementioned compounds in meaningful doses to prevent and inhibit the viral protein maturation of SARS-CoV-2.

However, in phase 392 after viral protein maturation 390, these viral proteins and new genomic RNA molecules 370 are assembled in the cytoplasm to form new infectious virus particles. Therefore, the inventive medicine aims to inhibit viral protein maturation so that as few new SARS-CoV-2 viruses would eventually be produced by the host cell. After assembly, those virus particles that eventually formed correctly despite the inventive medicine, are released from the cell by exocytosis and can initiate the infection cycle in new cells.

When phase 390 becomes inactive by the inhibiting effect of the inventive medicine, the virus production machine of the host cell cannot produce mature viral proteins, as SARS-CoV-2 viral protein maturation is inhibited in the host cell protein synthesis machinery.

These weak bases, vacuolar ATPase inhibitors and/or by ion channel modulators compounds are preferably locally administered to the patients by means of any of the following: Nasal drops, nasal sprays or aerosols targeted into lower respiratory pathway, either alone or in combinations. For example, in some embodiments the inventive medicine could be vaporized or provided as an aerosol through the air conditioning system or air ventilation system of a building, for example a hospital.

Even more preferably the weak bases, like ammonium salt, ammonium chloride, ammonium bicarbonate and chloroquine, vacuolar ATPase inhibitors, like bafilomycins and diphyllin, or ion channel modulators, like ivermectin of phases 360, 270 are mixed together with protease inhibitors, such as camostat and aprotinin, used in phase 130 of embodiment 10.

Thus, preferably the inventive medicine of this embodiment 30 is combined with cell membrane penetration inhibiting medicines of earlier embodiments 10 and 20. This will result in an inventive combined therapeutic effect on SARS-CoV-2 in the respiratory cell: Both the endosomic and non-endosomic pathways are blocked for SARS-CoV-2, and even if SARS-CoV-2 were somehow able to enter the cytoplasm, its protein maturation is inhibited in the host cell protein synthesis machinery by the inventive medicine.

Embodiment 30 can be readily combined with embodiments 10, 20, 40, 50, 60, 70, 80 and/or 90, because the intracellular and extracellular pathways described therein are in use simultaneously in a mammalian respiratory cell, in accordance with the invention.

In the next FIG. 4 we will discuss what embodiment 10 looks like anatomically.

This embodiment 40 FIG. 4 depicts at cellular level the non-endosomic virus entry to the cell from its binding to its release out of cell as an embodiment 40, and shows the impact site (inhibition site 1) of the inventive medicine for inhibiting the propagation of the SARS-CoV-2 virus in to the cell.

After virus 400 has contaminated subject's respiratory tract, it approaches the cell membrane 410 as illustrated in phases 100, 200, 300, settles and binds on cell surface 420 to cellular receptor as illustrated in phases 110, 120, 210, 220, 310, 320. In the case of SARS-Cov-2 virus, this happens through the interaction of virus S protein 430 and cellular receptor ACE2 440. After binding a non-endosomic entry can initiate as illustrated in phases 130, 230, 330.

In the non-endosomic pathway, as illustrated in phases 130, 330, proteases activate in pH independent manner the S protein fusion peptide, which directs the virus envelope to fuse 450 into cell membrane 410, as illustrated in phases

150, 170, 350. This fusion activation can be prevented at inhibition site 1 460 with proteinase inhibitors, such as camostat and aprotinin, as illustrated in phase 160. After fusion the virus 400 enters 470 into cellular cytoplasm and dissembles 480, releasing virus genome 481 (in the case of SARS-CoV-2 the genome is single stranded RNA), as illustrated in phases 180, 360.

The released virus genome 481 is then replicated 482 to new viral genomes 483 by cell's own machinery, as illustrated in phases 190, 370. At the same time, the revealed virus genome 481 also initiates the synthesis of viral proteins 485 by cell's own protein synthesis machinery 484, as illustrated in phases 191, 380. These proteins are synthesized in endoplasmic reticulum 486 and are transported into Golgi apparatus 487, where they mature to final proteins 488 at partly acidic conditions, as illustrated in phases 192, 390. After Golgi apparatus 487, the mature viral proteins 488 and the replicated new viral SARS-CoV-2 genomes 483 are assembled 489 to new virus particles 491, which are thereafter released from the cell by exocytosis 490, as illustrated in phases 193, 392.

The released viruses 491 can then infect new cells and start the infection cycle again. However, it is clearly apparent that the whole activity within the cell membrane 410

Embodiment 40 can be readily combined with embodiments 10, 20, 30, 50, 60, 70, 80 and/or 90, because the intracellular and extracellular pathways described therein are in use simultaneously in a mammalian respiratory cell, in accordance with the invention.

This FIG. 5 depicts at cellular level the endosomic virus entry to the cell from its binding to its release out of cell as an embodiment 50, and shows the impact site (inhibition site 2) of the inventive medicine for inhibiting the propagation of the virus into the cell.

After virus 500 has contaminated subject's respiratory tract, it approaches the cell membrane 510 as illustrated in phases 100, 200, 300, settles and binds 520 on cell surface to cellular receptor as illustrated in phases 110, 120, 210, 220, 310, 320. In the case of SARS-Cov-2 virus, this happens through the interaction of virus S protein 530 and cellular receptor ACE2 540. After binding, an endosomic entry of SARS-Cov-2 virus can initiate as illustrated in phases 140, 240, 340.

In endosomic pathway, as illustrated in phases 240, 340, after binding the virus 500 enters into cell by clathrin-mediated endocytosis 550, where the virus together with ACE2 receptor is uptaken into early endosome 560, as illustrated in phase 250. This early endosome later acidifies 570 by the function of lysosomes to late endosome 581, as illustrated in phase 260. This acidification can be inhibited at inhibition site 2 by the inventive medicine shown by 580. The inventive medicine causing the inhibiting effect at location 580 in the cell typically comprises any of the following: weak bases, proton pump inhibitors and ion channel inhibitors, as illustrated in phase 270.

After the acidification, proteinases, like cathepsin, activate virus S protein 530 fusion peptide, which through interaction with ACE2 receptor 540 fuses 582 to endosomal membrane, as illustrated in phase 280. After fusion, SARS-CoV-2 virus 500 enters 583 into cellular cytoplasm from the late endosome 581 and dissembles 584, releasing virus genome 585 single stranded RNA, as illustrated in phases 290, 360. This endosomal fusion through the cell membrane into the cytoplasm can be inhibited by the inventive medicine containing for example weak bases, like ammonium salt, ammonium chloride, ammonium bicarbonate and chloroquine, by vacuolar ATPase inhibitors, like bafilomycins and diphyllin, or by ion channel modulators, like ivermectin, in any combination or just individually and separately.

The released virus genome 585 is then replicated 586 to new viral genomes 587 by the cell's own machinery, as illustrated in phases 291, 370. At the same time, the revealed virus genome 585 also initiates the synthesis 588 of viral proteins 589 by cell's own protein synthesis machinery, as illustrated in phases 292, 380.

These proteins are synthesized in endoplasmic reticulum 590 and are transported into Golgi apparatus 591, where they maturate to final proteins 592 at partly acidic conditions, as illustrated in phases 293, 390. After Golgi apparatus 591, the mature viral proteins 592 and the replicated new viral SARS-CoV-2 genomes 587 are assembled 593 to new SARS-CoV-2 virus particles 595, which are thereafter released from the cell by exocytosis 594, as illustrated in phases 294, 392.

These released viruses 595 can then infect new cells and start the infection cycle again.

Embodiment 50 can be readily combined with embodiments 10, 20, 30, 40, 60, 70, 80 and/or 90, because the intracellular and extracellular pathways described therein are in use simultaneously in a mammalian respiratory cell, in accordance with the invention.

Figure 6:
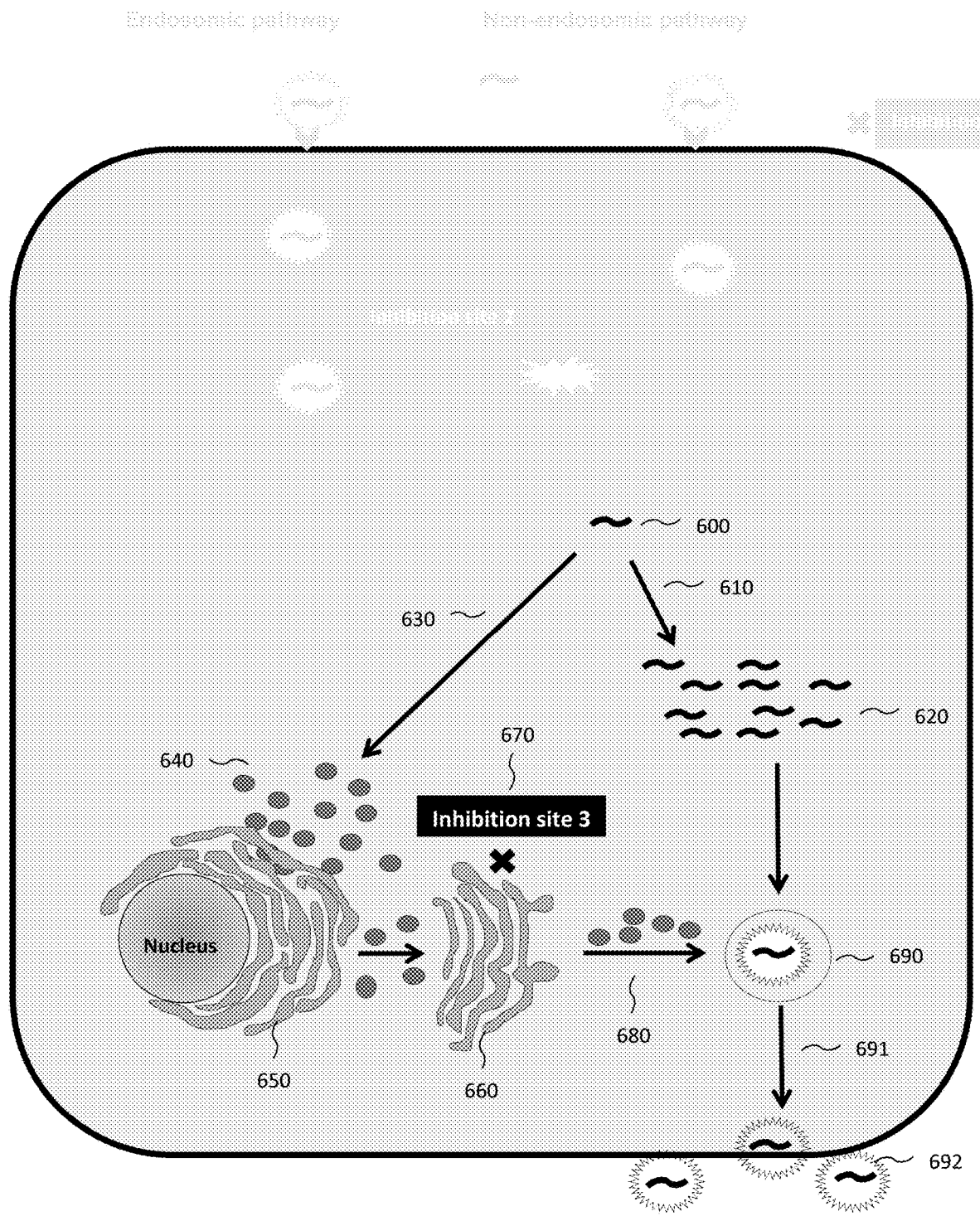

This FIG. 6 depicts at cellular level the intracellular viral pathway from the released virus genome to virus release out of cell as an embodiment 60, and shows the impact site (inhibition site 3) of the inventive medicine for inhibiting the propagation of the SARS-CoV-2 virus protein synthesis within the host cell.

After the virus genome 600 (in the case of SARS-CoV-2 the genome is single stranded RNA), either after non-endosomic entry, as illustrated in phases 130, 230, 330, or after endosomic entry, as illustrated in phases 140, 240, 340, has been released, as illustrated in phases 180, 290, 360, the virus genome 600 is replicated 610 to new viral genomes 620 by cell's own machinery, as illustrated in phases 190, 291, 370. At the same time, the revealed virus genome 600 also initiates the synthesis 630 of SARS-CoV-2 viral proteins 640 by cell's own protein synthesis machinery, as illustrated in phases 191, 292, 380. These proteins are synthesized in endoplasmic reticulum 650 and are transported into Golgi apparatus 660, where they maturate to final proteins 680 at partly acidic conditions, as illustrated in phases 192, 293, 390.

This maturation can be inhibited by the inventive medicine at inhibition site 3 670 with weak bases, proton pump inhibitors and ion channel inhibitors, as illustrated in phase 391. After Golgi apparatus 660, the mature viral proteins 680 and the replicated new viral genomes 620 are assembled 690 to new SARS-CoV-2 virus particles 692, which are thereafter released from the cell by exocytosis 691, as illustrated in phases 193, 294, 392.

The inventive medicinal component inhibiting the SARS-CoV-2 protein maturation within the host cell typically contains any of the following: weak bases, like ammonium salt, ammonium chloride, ammonium bicarbonate and chloroquine, vacuolar ATPase inhibitors, like bafilomycins and diphyllin, or ion channel modulators, like ivermectin in any combination or permutation.

The released viruses 692 can infect new cells and start the infection cycle again if the viral proteins are maturated, but with the inhibiting effect of the inventive medicine, this should not happen.

Interfering with the protein synthesis is likely to have greater side effects for patients than preventing the passage through the cell membrane of respiratory cells. Therefore, in some preferable embodiments the dose of the SARS-CoV-2 protein maturation inhibiting component 670 is kept lower, whereas dosage of the cell membrane passage inhibiting component 460, 580 is kept higher.

This might change the other way, if a new third extracellular SARS-CoV-2 pathway is discovered. Then it might be preferable to keep the dose of the SARS-CoV-2 protein maturation inhibiting component 670 higher, whereas dosage of the cell membrane passage inhibiting component 460, 580 is kept lower, or at sufficient level to block the two endosomal and non-endosomal pathways of embodiments 10 and 20.

Embodiment 60 can be readily combined with embodiments 10, 20, 30, 40, 50, 70, 80 and/or 90, because the intracellular and extracellular pathways described therein are in use simultaneously in a mammalian respiratory cell, in accordance with the invention.

Figure 7:
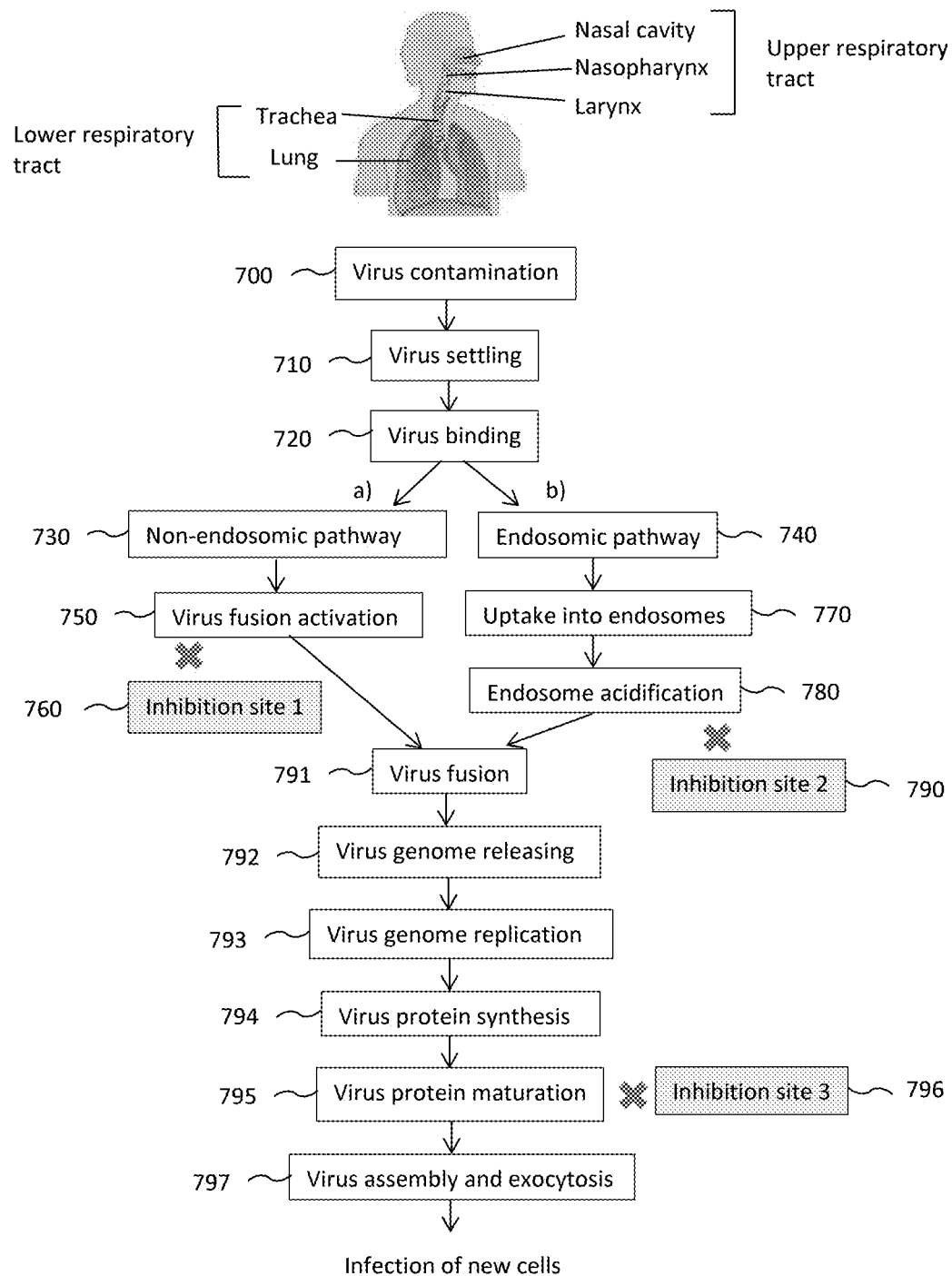

This FIG. 7 is a comprehensive presentation of SARS-CoV-2 virus entry pathways to the cell from its binding to its release out of the cell as an embodiment 70, and shows the impact sites (inhibition sites 1, 2 and 3) of the inventive medicine for inhibiting the propagation of the SARS-CoV-2 virus into the cell and within the cell.

In phase 700 the enveloped viruses, like SARS-CoV-2 coronavirus, enter and contaminate the respiratory track either via direct contact of fingers or other virus carrying surfaces or via inhaled air. Virus can enter nasopharyngeal area through nose, mouth or eyes having a direct contact to nasal cavity. From upper airways, it can emanate downwards in the respiratory tract, and in more severe cases into lungs causing pneumonia. In some cases, it can go even to stomach causing e.g. diarrhea.

In phase 710 after contamination 700 SARS-CoV-2 virus approaches and settles down on respiratory track mucosa. To initiate infection virus has to enter into the epithelial cells of the respiratory mucosa.

In phase 720 after settling 710 on the cell membrane, SARS-CoV-2 virus binds to a specific receptor on the surface of the respiratory track epithelial cells. Each enveloped SARS-CoV-2 virus has its own specific receptor for binding. For SARS-CoV-2 this receptor is ACE2 membrane protein. In the case of SARS-CoV-2, this binding happens through virus surface S protein (spike) and cell membrane ACE2 receptor interaction.

After SARS-CoV-2 virus binding 720 to cell membrane receptor, two pathways 730 and 740 are initiated: a) non-endosomic pathway 730 (endocytosis independent pathway) and b) endosomic pathway 740 (endocytosis dependent pathway).

In phase 750 in non-endosomic pathway (a) 730 membrane protease, e.g. transmembrane protease serine subfamily 2 (TMPRSS2), activates ACE2 receptor and virus S protein for fusion 791 in pH independent manner. This activation is inhibited by the inventive medicine at inhibition site 1 760 by protease inhibitors, which may include e.g. camostat and/or aprotinin or another protease inhibitor.

In phase 770 in endosomic pathway (b) 740 after SARS-CoV-2 virus has bound to ACE2 on cell membrane, ACE2/virus complex is transferred into an early endosome through a clathrin-mediated endocytosis.

In phase 780 within the cytoplasm, the early endosome is acidified and matures to late endosome. This acidification can be inhibited at inhibition site 2 790 by the inventive medicine. The inventive medicine may include: weak bases, like ammonium salt, ammonium chloride, ammonium bicarbonate and chloroquine, vacuolar ATPase inhibitors, like bafilomycins and diphyllin, and/or ion channel modulators, like ivermectin in any combination or permutation in accordance with the invention.

In phase 791 SARS-CoV-2 Virus nucleocapsid fuses to cell membranes by the aid of proteases. They activate a fusion peptide part of the virus S protein, which then fuses the virus envelope into the cell membrane. This activation happens either in pH independent way 170 to cell membrane or in pH dependent way 280 to endosomal membrane.

In phase 792 after fusion 791, SARS-CoV-2 virus nucleocapsids that survived the inhibiting effects of the medicine in phases 760 and 790 enter into cell cytoplasm and dissemble, whereby the non-inhibited SARS-CoV-2 virus genetic material is released. In the case of SARS-CoV-2 coronaviruses, the genetic material is a single-stranded RNA genome.

In phase 793 after genome releasing 792 of SARS-CoV-2 virus genome, it replicates by reverse transcriptase enzyme produced by host cell's protein synthesis machinery.

In phase 794 the viral proteins and RNA genome (in the case of SARS-CoV-2) are synthesized using host cell's own protein synthesis machinery. At this point virus 'kidnaps' for its use the whole protein producing capacity of the cell and most of the products synthesized are viral (proteins, RNA).

After viral protein synthesis 794 the viral proteins, synthesized from the non-inhibited SARS-CoV-2 virus kidnapping of the protein synthesis machinery, are matured in host cell's endoplasmic reticulum/Golgi compartment, e.g. by glycosylation. Some of these protein maturation reactions in Golgi apparatus are pH dependent (acidic). This maturation can be inhibited by the inventive medicine at inhibition site 3 796. The inventive medicine typically comprises weak bases, like ammonium bicarbonate and chloroquine. Also, vacuolar ATPase inhibitors, like bafilomycins and diphyllin, or ion channel modulators, like ivermectin, can be used in providing an inhibiting effect on viral protein maturation by the inventive medicine in this step.

In phase 797 after viral protein maturation 795, they and new genomic RNA molecules 793 are assembled in the cytoplasm to new infectious virus particles, if the dose of the inventive medicine in 796 is insufficient. In preferable embodiments the SARS-CoV-2 viral protein maturation is suppressed as much as possible within the constraints of the side effects that can be persevered by the patients in a short period. This period is typically a bit longer than the period of suspected exposure to SARS-CoV-2. After assembly, the SARS-CoV-2 virus particles would be released from the cell by exocytosis and can initiate the infection cycle in new cells.

Embodiment 70 can be readily combined with embodiments 10, 20, 30, 40, 50, 60, 80 and/or 90, because the intracellular and extracellular pathways described therein are in use simultaneously in a mammalian respiratory cell, in accordance with the invention.

Figure 8:
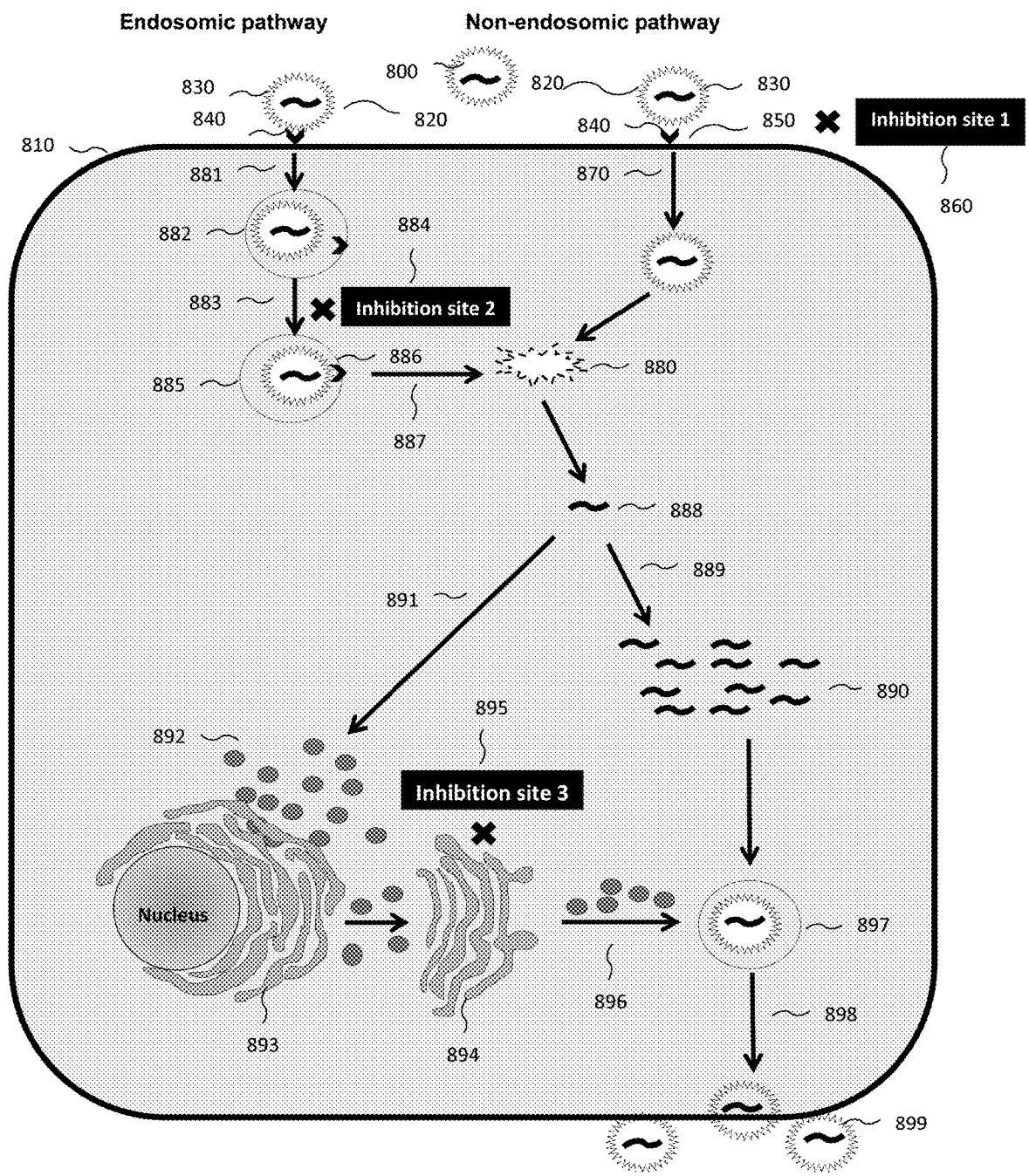

This FIG. 8 is a comprehensive presentation of virus entry pathways to the cell from its binding to its release out of the cell as an embodiment 80, and shows the impact sites (inhibition sites 1, 2 and 3) of the inventive medicine for inhibiting the propagation of the virus into the cell and within the cell.

After SARS-CoV-2 virus 800 has contaminated patient subject's respiratory tract, it approaches the cell membrane 810 as illustrated in phases 100, 200, 300, settles and binds 820 on cell surface to cellular receptor as illustrated in phases 110, 120, 210, 220, 310, 320, 420. In the case of SARS-Cov-2 virus, this happens through the interaction of virus S protein 830 and cellular receptor ACE2 840. After binding, two known pathways, a non-endosomic or endosomic entry, can initiate as illustrated in phases 130, 140, 230, 240, 330, 340, 730, 740. There might also be a third pathway for SARS-CoV-2 that we do not know yet.

In non-endosomic pathway, as illustrated in phases 130, 330, proteases activate in pH independent manner the S protein fusion peptide, which directs the SARS-CoV-2 virus envelope to fuse 850 into cell membrane 810, as illustrated in phases 150, 170, 350, 450. This fusion activation can be prevented by the inventive medicine at inhibition site 1 860 with proteinase inhibitors, as illustrated in phases 160, 460. After fusion, the virus 800 enters 870 into cellular cytoplasm and dissembles 880, releasing virus genome 888 (in the case of SARS-CoV-2 the genome is single stranded RNA), as illustrated in phases 180, 360, 480.

In endosomic pathway, as illustrated in phases 240, 340, after binding the virus 800 enters into cell by clathrin-mediated endocytosis 881, where the virus together with ACE2 receptor is uptaken into early endosome 882, as illustrated in phases 250, 350, 550. This early endosome later acidifies 883 by the function of lysosomes to late endosome 885, as illustrated in phases 260, 350, 570. This acidification can be inhibited by the inventive medicine at inhibition site 2 884 with weak bases, proton pump inhibitors and ion channel inhibitors, as illustrated in phases 270, 580. After acidification proteinases, like cathepsin, activate virus S protein 830 fusion peptide, which through interaction with ACE2 receptor 840 fuses 886 to endosomal membrane. After fusion, SARS-CoV-2 virus 800 enters 887 into cellular cytoplasm and dissembles 880, releasing virus genome 888 (in the case of SARS-CoV-2 the genome is single stranded RNA), as illustrated in phases 290, 360, 584.

The released SARS-CoV-2 virus genome 888 is then replicated 889 to new SARS-CoV-2 viral genomes 890 by cell's own machinery, as illustrated in phases 190, 291, 370, 482, 586. At the same time, the revealed SARS-CoV-2 virus genome 888 also initiates the synthesis 891 of viral proteins 892 by cell's own protein synthesis machinery, as illustrated in phases 191, 292, 380, 484, 588.

These proteins are synthesized in endoplasmic reticulum 893 and are transported into Golgi apparatus 894, where they maturate to final proteins 896 at partly acidic conditions, as illustrated in phases 192, 293, 390, 487, 591. This maturation step can be inhibited by the inventive medicine at inhibition site 3 895 with weak bases, proton pump inhibitors and ion channel inhibitors, as illustrated in phases 391, 670. After Golgi apparatus 894, the mature viral proteins 896 and the replicated new viral genomes 890 are assembled 897 to new virus particles 899, which are thereafter released from the cell by exocytosis 898, as illustrated in phases 193, 294, 392, 490, 594, 691. These released viruses 899 can then infect new cells and start the infection cycle again.

There are thus at least three identified locations (inhibition sites 1, 2 and 3) in the viral pathways of enveloped SARS-CoV-2 viruses that can be targeted by the inventive drug molecules. Inhibition site 1 is indicated in embodiment 10, phase 160; embodiment 40, phase 460; embodiment 70, phase 760; embodiment 80, phase 860. Inhibition site 2 is indicated in embodiment 20, phase 270; embodiment 50, phase 580; embodiment 70, phase 790; embodiment 80, phase 884. Inhibition site 3 is indicated in embodiment 30, phase 391; embodiment 60, phase 670; embodiment 70, phase 796; embodiment 80, phase 895.

The function of inhibition site 1 160, 460, 760, 860, can be targeted by protease inhibitors in the inventive medicine, for instance camostat and aprotinin.

The function of inhibition site 2 270, 580, 790, 884 can also be targeted by inhibitors of vesicular acidification in the same inventive medicine, which may include any of the following: weak bases like ammonium salt, ammonium chloride, ammonium bicarbonate and chloroquine, inhibitors of vacuolar ATPase, like bafilomycins, diphyllin, and/or modulators of ion channels, like ivermectin.

The function of inhibition site 3 391, 670, 796, 895 can also be targeted by inhibitors of vesicular acidification in the same inventive medicine, which may include any of the following: weak bases like ammonium salt, ammonium chloride, ammonium bicarbonate and/or chloroquine, inhibitors of vacuolar ATPase like bafilomycins, diphyllin, and/or modulators of ion channels, like ivermectin.

The corresponding locations, where the inventive medicine acts, anatomically within the host cell are believed to be the following:

Inhibition site 1: Fusion of virus to the plasma membrane, as illustrated in phases 170, 350, 450, 750, 850, can be inhibited by protease inhibitors, e.g. TMPRSS2 inhibitors (e.g. camostat and aprotinin).

Inhibition site 2: Inhibition of endosomal acidification, as illustrated in phases 260, 570, 780, 883, will prevent cathepsin activation and thus inhibit fusion of viral envelope to the endosomal membrane preventing release of viruses into the cytoplasm for replication of viral RNA. Acidification can be inhibited by weak bases (like chloroquine, ammonium), proton pump inhibitors (like bafilomycins), and chloride channel inhibitors (like ivermectin).

Inhibition site 3: When viral SARS-CoV-2 RNAs enter the endoplasmic reticulum, they are translated to viral SARS-CoV-2 proteins. These proteins are then transported into the Golgi compartment, where they are maturated, as illustrated in phases 192, 293, 390, 795, 487, 591, 660, 894, e.g. by glycosylation. Some of the reactions are pH dependent and can be inhibited by either weak bases (like ammonium, ammonium salt, ammonium chloride, ammonium bicarbonate and chloroquine), proton pump inhibitors (like bafilomycins), or chloride channel modulators (like ivermectin).

The inventive medicine uses these aforementioned compounds in any permutation or combination in local administration by any of the following: nasal drops, nasal sprays or aerosols targeted into lower respiratory pathway) either alone or in the following combinations. The inventive medicine prevents the viral infection and/or to treats the infection in its early phase by decreasing viral entry into epithelial cells by any of the following exemplary compositions:

1. Ammonium alone
2. Chloroquine alone
3. Ivermectin alone
4. Camostat alone
5. Aprotinin alone
6. Vacuolar proton pump inhibitors alone (bafilomycins)
7. or any of these in combinations of two or more drugs, for instance chloroquine and camostat, chloroquine and camostat and ivermectin, etc.

Embodiment 80 can be readily combined with embodiments 10, 20, 30, 40, 50, 60 and/or 70 because the intracellular and extracellular pathways described therein are in use simultaneously in a mammalian respiratory cell, in accordance with the invention.

Clause 1. A medicine for COVID-19, characterized in that, the medicine is a pH increase inducing agent, and said medicine is administered to a patient to inhibit endosomal acidification (260) preventing cathepsin activation and thus inhibit fusion of viral envelope to the endosomal membrane preventing release of SARS-CoV-2 viruses into the cytoplasm and the consequent replication of SARS-CoV-2 virus RNA in the mammalian respiratory cell.

Clause 2. A medicine as claimed in clause 1, characterized in that, the medicine comprises any of the following: chloroquine, chloroquine phosphate and/or hydroxychloroquine phosphate and/or chloroquine phosphate and/or chloroquine sulphate and/or hydroxychloroquine sulphate.

Clause 3. A medicine as claimed in clause 1, characterized in that, the medicine is used as a prophylactic.

Clause 4. A medicine as claimed in clause 1, characterized in that, the medicine comprises any of the following: weak base, ammonium salt, ammonium chloride, ammonium bicarbonate, proton pump inhibitor, bafilomycin, and/or chloride channel inhibitor, ivermectin.

Clause 5. A medicine for COVID-19, characterized in that, the medicine comprises at least one protease inhibitor arranged to inhibit the fusion of the SARS-CoV-2 virus through the plasma membrane (150) of a mammalian respiratory cell.

Clause 6. A medicine as claimed in clause 5, characterized in that, the protease inhibitors can be any of the following: TMPRSS2 inhibitors, camostat and/or aprotinin.

Clause 7. A medicine for COVID-19, characterized in that, the medicine is arranged to target viral RNAs in the endoplasmic reticulum, and the viral RNAs are arranged to be translated to viral proteins, and the viral proteins are arranged to be transported into the Golgi compartment of the mammalian respiratory cell, where the viral proteins are arranged to be glycosylated, and the medicine is arranged to inhibit any of the preceding reactions and/or arranged to inhibit proton pumps (390).

Clause 8. A medicine as claimed in clause 7, characterized in that, the medicine comprises any of the following: weak bases, ammonium, ammonium salt, ammonium chloride, ammonium bicarbonate, chloroquine, and/or proton pump inhibitor, bafilomycin.

Clause 9. A medicine for COVID-19, characterized in that, the medicine is a pH increase inducing agent, and said medicine is administered to a patient to inhibit endosomal acidification (260) preventing cathepsin activation and thus inhibit fusion of viral envelope to the endosomal membrane preventing release of SARS-CoV-2 viruses into the cytoplasm and the consequent replication of SARS-CoV-2 virus RNA in the mammalian respiratory cell, and the medicine comprises protease inhibitors arranged to inhibit the fusion of the SARS-CoV-2 virus through the plasma membrane (150) of a mammalian respiratory cell, and the medicine is arranged to target viral RNAs in the endoplasmic reticulum, and the viral RNAs are arranged to be translated to viral proteins, and the viral proteins are arranged to be transported into the Golgi compartment of the mammalian respiratory cell, where the viral proteins are arranged to be glycosylated, and the medicine is arranged to inhibit any of the preceding reactions and/or arranged to inhibit proton pumps (390).

Clause 10. A medicine as claimed in clause 9, characterized in that, the medicine comprises any of the following: chloroquine, chloroquine phosphate and/or hydroxychloroquine phosphate and/or chloroquine phosphate and/or chloroquine sulphate and/or hydroxychloroquine sulphate, proton pump inhibitor, bafilomycin, and/or chloride channel inhibitor, ivermectin, protease inhibitors, TMPRSS2 inhibitors, camostat and/or aprotinin, weak bases, ammonium salt, ammonium chloride, ammonium bicarbonate, ammonium, chloroquine.

Clause 11. A medicine as claimed in clause 1, characterized in that the method of administration of each compound could be any of the following:
Nasal drops
Nasal lavage
Nasal spray
Inhaled aerosol, and/or
applied as gas in inhaled air Clause 12. A medicine as claimed in clause 5, characterized in that the method of administration of each compound could be any of the following:
Nasal drops
Nasal lavage
Nasal spray
Inhaled aerosol, and/or
applied as gas in inhaled air.

Clause 13. A medicine as claimed in clause 7, characterized in that the method of administration of each compound could be any of the following:
Nasal drops
Nasal lavage
Nasal spray
Inhaled aerosol, and/or
applied as gas in inhaled air.

Clause 14. A medicine as claimed in clause 9, characterized in that the method of administration of each compound could be any of the following:
Nasal drops
Nasal lavage
Nasal spray
Inhaled aerosol, and/or
applied as gas in inhaled air.

Clause 15. A medicine as claimed in clause 1, characterized in that the medicine dosage is 1-10% of the maximal systemic dosage of each compound for a patient.

Clause 16. A medicine as claimed in clause 5, characterized in that the medicine dosage is 1-10% of the maximal systemic dosage of each compound for a patient.

Clause 17. A medicine as claimed in clause 7, characterized in that the medicine dosage is 1-10% of the maximal systemic dosage of each compound for a patient.

Clause 18. A medicine as claimed in clause 9, characterized in that the medicine dosage is 1-10% of the maximal systemic dosage of each compound for a patient.

Clause 19. A medicine as claimed in clause 5, characterized in that, the medicine is used as a prophylactic.

Clause 20. A medicine as claimed in clause 7, characterized in that, the medicine is used as a prophylactic.

Clause 21. A medicine as claimed in clause 9, characterized in that, the medicine is used as a prophylactic.

The invention has multiple advantages. Using local administration and especially more than one drug at the same time in the inventive medicine, it is possible to reduce the total dosage and decrease serious side effects known to be associated to each of above-mentioned drugs and still protect patients from COVID-19.

Method of administration of each compound and the inventive medicine could include any of the following exemplary drug delivery methods:

1. Nasal drops
2. Nasal lavage
3. Nasal spray
4. Inhaled aerosol
5. In addition, ammonium could be applied as gas in air inhaled by the patients.

In some exemplary embodiments of dosage of the inventive medicine, 1-10% of the maximal systemic dosage of each compound will be used.

The inventive medicine has been explained with reference to the earlier embodiments. However, the invention is not limited to these medicines and therapeutic uses but comprises all medicines within the spirit and scope of the inventive idea, and the claims that follow.

The invention claimed is:

1. An intranasal COVID-19 medicine, comprising the combination of:
   aprotinin;
   hydroxychloroquine phosphate or hydroxychloroquine sulfate; and
   ivermectin.

2. An intranasal COVID-19 medicine, comprising the combination of:
   aprotinin;
   hydroxychloroquine phosphate or hydroxychloroquine sulfate; and
   bafilomycin.

3. An intranasal COVID-19 medicine, comprising the combination of:
   aprotinin;
   hydroxychloroquine phosphate or hydroxychloroquine sulfate;
   ivermectin; and
   bafilomycin.

4. An intranasal COVID-19 medicine, comprising the combination of:
   aprotinin;
   ammonium salt; and
   one or more of ivermectin or bafilomycin.

* * * * *